United States Patent [19]

Dubief

[11] Patent Number: 5,536,493
[45] Date of Patent: Jul. 16, 1996

[54] COMPOSITION FOR WASHING KERATINOUS MATERIALS IN PARTICULAR HAIR AND/OR SKIN

[75] Inventor: Claude Dubief, Le Chesnay, France

[73] Assignee: L'Oreal, Paris, France

[21] Appl. No.: 181,958

[22] Filed: Jan. 18, 1994

Related U.S. Application Data

[63] Continuation of Ser. No. 964,107, Oct. 20, 1992, abandoned, which is a continuation of Ser. No. 595,979, Oct. 11, 1990, abandoned.

[30] Foreign Application Priority Data

Oct. 13, 1989 [FR] France .................. 89 13459

[51] Int. Cl.$^6$ .................. A61K 7/06; A61K 7/48
[52] U.S. Cl. .................. 424/70.13; 424/70.12; 424/70.121; 424/70.22; 424/70.24; 424/70.23; 424/70.19
[58] Field of Search .................. 424/70, 71, 401, 424/70.12, 70.121, 70.13, 70.22, 70.24, 70.19, 70.23

[56] References Cited

U.S. PATENT DOCUMENTS

| | | | |
|---|---|---|---|
| 2,826,551 | 3/1958 | Geen | 252/174.15 |
| 3,659,025 | 4/1972 | Halleck | 514/777 |
| 4,364,837 | 12/1982 | Pader | 252/174.15 |
| 4,465,619 | 8/1984 | Baskamp | 252/DIG. 2 |
| 4,519,844 | 5/1985 | Chaux et al. | 106/209 |
| 4,704,272 | 11/1987 | Oh et al. | 252/174.15 X |
| 4,736,756 | 4/1988 | Grollier | 424/DIG. 4 |
| 4,741,855 | 5/1988 | Grote et al. | 252/174.15 X |
| 4,744,978 | 5/1988 | Homan et al. | 424/70 |
| 4,749,565 | 6/1988 | Grollier | 8/405 X |
| 4,788,006 | 11/1988 | Bolish, Jr. et al. | 252/DIG. 13 |
| 4,820,512 | 4/1989 | Grollier | 514/63 X |
| 4,824,602 | 4/1989 | Juneja | 424/70 X |
| 4,842,850 | 6/1989 | Vu | 252/DIG. 13 |
| 4,851,154 | 7/1989 | Grollier et al. | 252/DIG. 13 |
| 4,871,530 | 10/1989 | Grollier et al. | 252/DIG. 13 |
| 4,885,296 | 12/1989 | Manoury et al. | 514/252 |
| 4,902,499 | 2/1990 | Bolish, Jr. et al. | 252/DIG. 13 |
| 4,904,275 | 2/1990 | Grollier | 8/406 X |
| 4,916,133 | 4/1990 | Manoury et al. | 514/252 |
| 4,925,659 | 5/1990 | Grollier et al. | 424/47 X |

FOREIGN PATENT DOCUMENTS

| | | | |
|---|---|---|---|
| 0074264 | 3/1983 | European Pat. Off. | A61K 7/08 |
| 0331915 | 9/1989 | European Pat. Off. | |
| 2188060 | 9/1987 | United Kingdom . | |
| 2194734 | 3/1988 | United Kingdom | A61K 7/060 |
| 2211192 | 6/1989 | United Kingdom . | |

*Primary Examiner*—Thurman K. Page
*Assistant Examiner*—Sally Gardner
*Attorney, Agent, or Firm*—Jacobson, Price, Holman & Stern

[57] ABSTRACT

Composition for washing keratinous materials, in particular hair and/or the skin, characterized in that it contains, in an aqueous medium, at least one silicone insoluble in this medium, at least one anionic, nonionic or amphoteric detergent surfactant and at least one scleroglucan optionally treated with glyoxal.

23 Claims, No Drawings

COMPOSITION FOR WASHING KERATINOUS MATERIALS IN PARTICULAR HAIR AND/OR SKIN

This is a continuation of application Ser. No. 07/964,107, filed Oct. 20, 1992; now abandoned which in turn is a continuation application of Ser. No. 07/595,979, filed Oct. 11, 1990, abandoned.

The present invention relates to compositions for washing keratinous materials, such as, more particularly, hair and/or the skin, and comprising, in an aqueous medium, at least one silicone, one surfactant and one scleroglucan optionally treated with glyoxal, as well as the washing procedure using these compositions.

The compositions for washing keratinous materials are well known in the state of the art.

In particular, it has already been proposed to use such compositions additionally containing surfactant and silicones.

Such compositions are also known containing, as suspending and thickening agents, crosslinked polyacrylic acids such as, in particular, the products sold under the name Carbopol, celluloses such as hydroxypropylcellulose, or xanthan gum.

However, these suspending and thickening agents present some problems, in particular because of the fact that the compositions containing them sometimes have an inadequate stability due, in particular, to poor compatibility with the surfactants customarily used in the washing compositions.

It has also been found that the cosmetic properties of such compositions, and in particular shampoos, were inadequate. Thus, on using crosslinked polyacrylic acids or cellulose derivatives as suspending and thickening agents a phase separation is often found leading to heterogeneous and unstable shampoos.

The compositions containing xanthan gum have inadequate detergent properties.

For this reason, compositions for washing keratinous materials and more particularly the skin and hair are sought which have good stability properties and confer valuable cosmetic properties to the materials treated, while having good detergent properties.

The Applicant has discovered, and this is the subject of the invention, that by using a scleroglucan optionally treated with glyoxal in washing compositions based on insoluble silicones defined below and detergent surfactants, the compositions had a very good homogeneity, a very fine particle size distribution and a good stability over time.

Moreover, these compositions confer great softness to the hair and/or the skin and have improved detergent properties.

In addition to their washing properties, these compositions have hair-conditioning properties, that is to say that the treated hair has a sheen, is easy to comb and soft to the touch.

The invention therefore relates to such washing compositions which are based on silicones defined below, detergent surfactants and scleroglucans, are homogeneous and stable over time and have good detergent properties while conferring softness to the materials treated.

Another subject of the invention consists in the washing procedure using such compositions.

Further subjects of the invention will become apparent on reading the description and the examples which follow.

The compositions for washing keratinous materials and in particular hair and the skin, according to the invention, comprise, in an aqueous medium, at least one silicone, at least one anionic, nonionic or amphoteric surfactant having detergent properties, at least one scleroglucan, optionally treated with glyoxal, and at least one silicone which is insoluble in the aqueous medium, not reactive with the latter and is in the form of oils, resins or gums and chosen from:
A) the volatile silicones having a boiling point between 60° C. and 260° C., and
B) non-volatile silicones chosen, in particular, from polyalkylsiloxanes, polyarylsiloxanes, polyalkylarylsiloxanes, unmodified or organo-modified polyethersiloxane copolymers, silicone gums and resins, some organo-modified polysiloxanes and their mixtures.

The volatile silicones are more particularly chosen from:
a) the cyclic silicones containing from 3 to 7 silicon atoms and preferably 4 to 5 silicon atoms, such as, more particularly, octamethylcyclotetrasiloxane, sold under the name VOLATILE SILICONE 7207 by UNION CARBIDE or SILBIONE 70045 V 2 sold by RHONE POULENC, or decamethylcyclopentasiloxane, sold under the name VOLATILE SILICONE 7158 by UNION CARBIDE, or SILBIONE 70045 V 5, sold by RHONE POULENC, as well as their mixtures.

The cyclopolymers such as dimethylsiloxane/methylalkylsiloxane and in particular the volatile silicone FZ 3109, sold by UNION CARBIDE, having the structure:

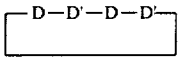

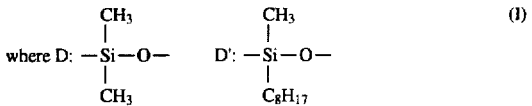

may also be mentioned.
b) the straight-chain volatile silicones having 2 to 9 silicon atoms and having a viscosity of less than or equal to $5 \times 10^{-6}$ m$^2$/s at 25° C. Silicones of this type are, in particular, hexamethyldisiloxane, sold under the name SILBIONE 70 041 V 0.65 by RHONE POULENC. Silicones belonging to this category are also described in the article published in Cosmetics and toiletries, Vol. 91, Jan. 76, p. 27–32—TODD & BYERS, "Volatile Silicone fluids for cosmetics".

The non-volatile silicones mentioned above are chosen, more particularly, from the polyalkylsiloxanes, amongst which the straight-chain polydimethylsiloxanes containing trimethylsilyl end groups and having a viscosity of $5 \times 10^{-6}$ to 2.5 m$^2$/s at 25° C., preferably $1 \times 10^{-5}$ to 1 m$^2$/s, may principally be mentioned.

Amongst these polyalkylsiloxanes, the following commercial products may be mentioned, by way of non-limiting example:
the SILBIONE oils of the series 70 047 and 47, marketed by RHONE POULENC, such as 47 V 500,000 oil from RHONE POULENC;
the 200 series oils from DOW CORNING;
the VISCASIL oils from GENERAL ELECTRIC and some SF series oils (SF 96, SF 18) from GENERAL ELECTRIC.

The straight-chain polydimethylsiloxanes containing trihydroxysilyl end groups may also be mentioned, such as, more particularly, the series 48 V oils from RHONE POULENC.

In this category of polyalkylsiloxanes, the products sold under the names ABIL WAX 9800 and 9801 by GOLDSCHMIDT, which are poly($C_1$–$C_{20}$)alkylsiloxanes, may be mentioned.

Amongst the polyalkylarylsiloxanes, the straight-chain and/or branched polymethylphenylsiloxanes and polydimethyldiphenylsiloxanes, having a viscosity of $1 \times 10^{-5}$ to $5 \times 10^{-2}$ m$^2$/s at 25° C., may be mentioned.

Amongst these polyalkylarylsiloxanes, the following commercial products may be mentioned for example and without limitation:

the 70 641 series SILBIONE oils from RHONE POULENC, such as the SILBIONE 70 641 V 30 and 70 641 V 200 oils from RHONE POULENC;

the RHODORSIL 70 633 V 30 and 763 oils from RHONE POULENC;

DC 556 Cosmetic Grade Fluid oil from DOW CORNING;

the PK series silicones from BAYER, such as the product PK20;

the PN and PH series silicones from BAYER, such as the products PN 1000 and PH 1000;

some SF series oils from GENERAL ELECTRIC, such as the products SF 1023, SF 1154, SF 1250 and SF 1265.

Amongst the unmodified or modified polyethersiloxane copolymers, the copolymers of ethylene oxide and/or propylene oxide with a diorganosiloxane may be mentioned, such as, more particularly, the product termed dimethiconecopolyol, sold by DOW CORNING under the name DC 1248, and $(C_{12})$alkylmethiconecopolyol, sold by DOW CORNING under the name Q2 5200; and the SILWET L 722, L 7500, L 77, L 711 oils from UNION CARBIDE.

The silicone gums which can be used according to the invention are polydiorganosiloxanes having high molecular weights of between 200,000 and 1,000,000, used on their own or as a mixture in a solvent. This solvent can be chosen from the volatile silicones defined above, the polydimethylsiloxane (PDMS) oils, the polyphenylmethylsiloxane (PPMS) oils, isoparaffins, methylene chloride, pentane, dodecane, tridecane, tetradecane or their mixtures.

The following products may be mentioned by way of example: the poly(dimethylsiloxane/methylvinylsiloxane), poly(dimethylsiloxane/diphenylsiloxane), poly(dimethylsiloxane/phenylmethylsiloxane) and poly(dimethylsiloxane/diphenylsiloxane/methylvinylsiloxane) gums.

The products which can be used more particularly are mixtures, such as:

the mixtures formed from a polydimethylsiloxane hydroxylated at the end of the chain (termed dimethiconol according to the nomenclature of the CTFA dictionary) and a cyclic polydimethylsiloxane (termed cyclomethicone according to the nomenclature of the CTFA dictionary), such as the product Q2 1401 sold by DOW CORNING.

the mixtures formed from a polydimethylsiloxane gum with a cyclic silicone, such as the product SF 1214 Silicone Fluid from GENERAL ELECTRIC (which is a SE 30 gum, corresponding to a dimethicone, having a molecular weight of 500,000 dissolved in the silicone SF 1202 Silicone Fluid (corresponding to decamethylcyclopentasiloxane)).

the mixtures of two PDMS of different viscosities, in particular a PDMS gum and a PDMS oil, such as the products SF 1236 and CF 1241 from GENERAL ELECTRIC. The product SF 1236 is the mixture of a SE 30 gum defined above, having a viscosity of 20 m$^2$/s, and a SF 96 oil having a viscosity of $5 \cdot 10^{-6}$ m$^2$/s (15% of SE 30 gum and 85% of SF 96 oil).

The product CF 1241 is the mixture of a SE 30 gum (33%) and a PDMS (67%), of viscosity $10^{-3}$ m$^2$/s.

The organopolysiloxane resins which can be used according to the invention are crosslinked siloxane systems containing $R_2SiO_{2/2}$, $RSiO_{3/2}$ and $SiO_{4/2}$ units, in which units R represents a hydrocarbon group having 1 to 6 carbon atoms or a phenyl group. Amongst these products, those particularly preferred are those in which R denotes a lower alkyl radical or a phenyl radical.

Amongst these resins, those which may be mentioned are the products sold under the name DOW CORNING 593 or those which are sold under the names SILICONE FLUID SS 4230 and SS 4267 by GENERAL ELECTRIC and which are "dimethyl/trimethylpolysiloxane".

The organo-modified silicones are silicones defined above and containing in their structure one or more organo-functional groups fixed directly to the siloxane chain or fixed via a hydrocarbon radical, these groups being chosen from:

1) thiol groups, such as the products GP 72 A and GP 71 from GENESEE,
2) carboxylate groups, as is the case for the products described in the CHISSO CORPORATION Patent EP-A-186,507,
3) alkoxy groups, such as the products sold under the name Silicone copolymer F-755 by SWS SILICONES, and ABIL WAX 2428, 2434 and 2440 from GOLDSCHMIDT,
4) hydroxyl groups, such as the polyorganosiloxanes containing a hydroxyalkyl group which are described in French Patent Application No. 85/16,334 and correspond to the formula:

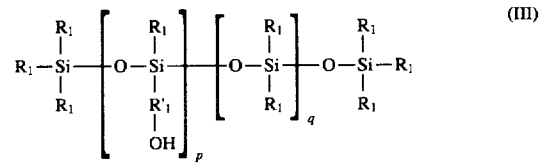

in which:

the radicals $R_1$, which are identical or different, are chosen from methyl and phenyl radicals, at least 60 mole % of the radicals $R_1$ denoting methyl;

the radical $R'_1$ is a $C_2$–$C_{18}$ divalent hydrocarbon alkylene member;

p is between 1 and 30 inclusive; and q is between 1 and 150 inclusive;

5) acyloxyalkyl groups, such as, for example, the polyorganosiloxanes described in Patent Application FR-A 88/17,433, corresponding to the formula:

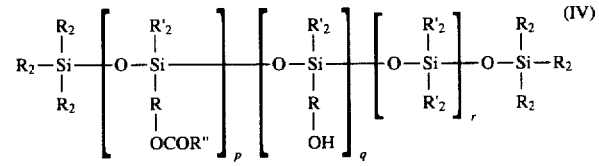

in which:

$R_2$ denotes a methyl, phenyl, —OCOR" or hydroxyl group and only one of the radicals $R_2$ per silicon atom may be OH;

$R'_2$ denotes methyl or phenyl, at least 60 mole % of the radicals $R_2$ and $R'_2$ as a whole denoting methyl;

R" denotes a $C_8$–$C_{20}$ alkyl or alkenyl;

R denotes a straight-chain or branched, $C_2$–$C_{18}$ divalent hydrocarbon alkylene radical;

r is between 1 and 120 inclusive;

p is between 1 and 30; and q is 0 or is less than 0.5 p, p+q being between 1 and 30; the polyorganosiloxanes of formula (IV) being able to contain

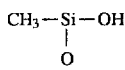

groups in proportions not exceeding exceeding 15% of the sum p+q+r.

The compounds of formula (IV) may be prepared by esterification of polyorganosiloxanes containing a hydroxyalkyl group, of formula (III) above.

The esterification takes place in a known manner, with an acid R"COOH or the acid anhydride, at a temperature of between 100° and 250° C., if appropriate in the presence of a catalyst such as aluminium chloride or zinc chloride or of a strong acid, such as hydrochloric acid or sulphuric acid.

A transesterification can also be carried out by heating a methyl ester of formula R"COOCH$_3$ and a diorganopolysiloxane of formula (III) to 100°–150° C. in the presence of an acid catalyst such as paratoluenesulphonic acid or an acid earth of montmorillonite type (KATALYSATOR KSF/0, sold by SUD-CHEMIE—A.G. MUNICH).

6) anionic groups of the carboxylic type, such as alkylcarboxylic groups, such as those present in the product X-22-3701E from SHIN-ETSU; 2-hydroxyalkylsulphonate; 2-hydroxyalkylthiosulphate, such as the products sold by GOLDSCHMIDT under the names "ABIL S201" and "ABIL S 255".

The polyorganosiloxanes more particularly preferred according to the invention are non-voltatile silicones chosen from the family of straight-chain polyalkylsiloxanes containing trimethylsilyl end groups, such as the products sold under the name SILBIONE 70047 and 47 V 500,000 by RHONE POULENC, or the polyalkylarylsiloxanes such as the oil SILBIONE 70641 V 200 marketed by RHONE POULENC;

mixtures of organosiloxanes and cyclic silicones, such as the product Q2 1401 sold by DOW CORNING and the product SF 1214 sold by GENERAL ELECTRIC;

the organopolysiloxane resin sold under the name DOW CORNING 593.

The mixture of two PDMS of different viscosities, such as the products sold under the name CF 1241 by GENERAL ELECTRIC, is used particularly preferentially.

The scleroglucans used according to the invention are neutral polysaccharides of microbial origin, obtained by aerobic fermentation of a glucose medium by a mushroom of the Sclerotium type and having the structure of a homopolymer of D-glucopyranose.

The scleroglucans correspond to the formula:

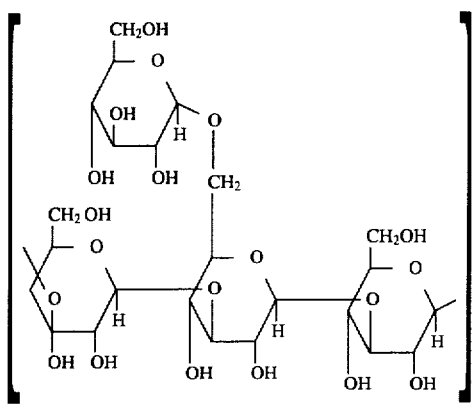

where n (degree of polymerization) varies from 500 to 1,600.

The scleroglucans more particularly used according to the invention are represented by the products sold under the name ACTIGUM CS by SANOFI BIO INDUSTRIES, and in particular ACTIGUM CS 11, and under the name AMIGEL by ALBAN MULLER INTERNATIONAL.

Other scleroglucans, such as that treated with glyoxal described in French Patent Application No. 2,633,940, can also be used.

The surfactants used in the compositions according to the invention are chosen from anionic, amphoteric, zwitterionic and nonionic surfactants or their mixtures.

Amongst the anionic surfactants, those which may be mentioned more particularly are the alkali metal salts, the ammonium salts, the amine salts or the aminoalcohol salts of the following compounds:

alkyl sulphates, alkyl ether-sulphates, alkylamide ether-sulphates, alkanolamide sulphates, alkylarylpolyether-sulphates and monoglyceride sulphates;

alkylsulphonates, alkylarylsulphonates, alkyl amidesulphonates, olefinsulphonates and paraffin-sulphonates;

alkyl sulphosuccinates, alkyl ether-sulphosuccinates and alkylamide sulphosuccinates;

alkyl sulphosuccinamates;

alkyl sulphoacetates;

alkyl phosphates and alkyl ether-phosphates; and acyl sarcosinates, acyl polypeptidates, acyl isethionates and N-acyltaurates.

The alkyl or acyl radical of these various compounds generally consists of a carbon chain containing 12 to 20 carbon atoms.

Amongst the anionic surfactants, the following may also be mentioned: the salts of fatty acids, such as oleic, ricinoleic, palmitic and stearic acids; the acids of copra oil or hydrogenated copra oil; and acyl lactylates in which the acyl radical contains 8 to 20 carbon atoms.

Amongst the nonionic surfactants, the following may be mentioned: polyoxyethylenated, polypropoxylated or polyglycerolated fatty alcohols, alkylphenols and acids having a fatty chain containing 8 to 18 carbon atoms, the number of ethylene oxide and propylene oxide groups being between 2 and 50 and the number of glycerol groups being between 2 and 30.

The following may also be mentioned: copolymers of ethylene oxide and propylene oxide, condensation products of ethylene oxide and propylene oxide with fatty alcohols, polyethoxylated fatty amides (preferably containing 2 to 30 moles of ethylene oxide), polyethoxylated fatty amines (preferably containing 2 to 30 moles of ethylene oxide), ethanolamides, glycol fatty acid esters, sorbitan fatty acid esters, which may or may not be oxyethylenated (preferably containing 2 to 30 moles of ethylene oxide), sucrose fatty acid esters, polyethylene glycol fatty acid esters, phosphoric triesters, fatty acid esters of glucose derivatives, amine oxides such as alkylamine oxides or N-acylamidopropylmorpholine oxides.

The preferred polyoxyethylenated or polyglycerolated fatty alcohols are oxyethylenated oleyl alcohol containing 10 moles of ethylene oxide, oxyethylenated lauryl alcohol containing 12 moles of ethylene oxide, oxyethylenated nonylphenol containing 9 moles of ethylene oxide, and polyglycerolated oleyl alcohol containing 4 moles of glycerol; the preferred oxyethylenated sorbitan fatty acid ester is polyoxyethylenated sorbitan monolaurate containing 20 moles of ethylene oxide.

Other compounds belonging to this category are compounds corresponding to the formulae (VI) to (VIII) below and/or prepared by the processes described below.

a) 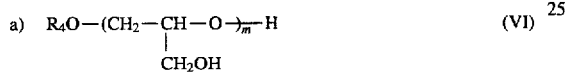 (VI)

in which $R_4$ denotes an alkyl radical containing 10 to 14 carbon atoms or a mixture of such radicals and m is an integer or decimal number from 2 to 10 and preferably from 3 to 6. These compounds can be prepared by the process described in the Patent FR-A-1,477,048;

b) $R_5$—CONH—$CH_2$—$CH_2$—O—$CH_2$—$CH_2$—O—($CH_2$—CHOH—$CH_2$—O)$_n$H (VII) in which $R_5$ denotes an alkyl and/or alkenyl radical having from 11 to 17 carbon atoms, or a mixture of such radicals, and n denotes an integer or decimal number from 1 to 5 and preferably from 1.5 to 4. These compounds of formula (VII) can be prepared by the process described in the Patent FR-A-2,328,763;

c) $R_6$—CHOH—$CH_2$—O—($CH_2$—CHOH—$CH_2$—O)$_p$—H (VIII) in which $R_6$ denotes an aliphatic, cycloaliphatic or arylaliphatic radical, preferably having 7 to 21 carbon atoms, and their mixtures, the aliphatic chains denoting, in particular, alkyl chains which can contain 1 to 6 ether, thioether and/or hydroxymethylene groups, and p is between 1 and 10 inclusive.

These compounds are prepared by a condensation reaction, under alkaline catalysis, of 2 to 10 and preferably 2.5 to 6 moles of glycidol with a $C_{10}$–$C_{14}$ alpha-diol or a mixture of $C_{10}$–$C_{14}$ alpha-diols, at a temperature of 120° to 180° C. and preferably of 140° to 160° C., the glycidol being added slowly, in accordance with the process described in the patent FR-A-2,091,516;

d) the compounds prepared by a condensation reaction, under acid catalysis, of 2 to 10 and preferably 2.5 to 6 moles of glycidol per mole of alcohol or alpha-diol containing 10 to 14 carbon atoms at a temperature of 50° to 120° C., the glycidol being added slowly to the alcohol or to the alpha-diol. The process for the preparation of these compounds is described more particularly in the Patent FR-A-2,169,787;

e) the poly(hydroxypropyl ether) compounds prepared by polyaddition of glycerol monochlorohydrin to an organic polyhydroxy compound, in the presence of a strong base, with removal of the water by distillation at the rate at which it is formed, described more particularly in the Patent FR-A-2,574,786.

Amongst the nonionic surfactants of the family of polyhydroxypropyl ethers described in paragraphs (a) to (e) above, the preferred compounds are represented by the formulae:

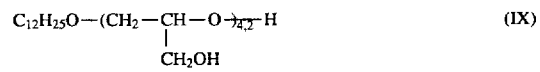 (IX)

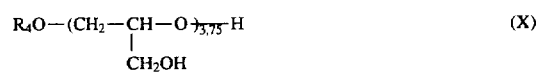 (X)

in which $R_4$ denotes a mixture of $C_{10}H_{21}$ and $C_{12}H_{25}$ alkyl radicals;

the compounds prepared by a condensation reaction, under alkaline catalysis, of 3.5 moles of glycidol with an alphadiol having 12 carbon atoms, in accordance with the process described in the Patent FR-A-2,091,516;

the compounds corresponding to the formula: $R_6$—CONH—$CH_2$—$CH_2$—O—$CH_2$—$CH_2$—O—($CH_2$—CHOH—$CH_2$—O)$_{3.5}$—H (XI) in which $R_6$ denotes a mixture of radicals comprising the following alkyl and alkenyl radicals: $C_{11}H_{23}$, $C_{13}H_{27}$, the radicals derived from copra fatty acids and the radical derived from oleic acid.

The compounds prepared by a condensation reaction of 3.5 moles of glycidol with a mixture of $C_{11}$–$C_{14}$ alphadiols, described more particularly in the Patent FR-A-2,091,516, and the poly(hydroxypropyl ether) obtained by a condensation reaction of glycerol monochlorohydrin (2.5 moles), in the presence of sodium hydroxide, with dodecane-1,2-diol are more particularly preferred.

The amphoteric and zwitterionic surfactants are chosen from the derivatives of secondary or tertiary aliphatic amines in which the aliphatic radical is a straight or branched chain containing from 8 to 18 carbon atoms and which contain at least one anionic carboxyl, sulphonate, sulphate, phosphate or phosphonate group conferring solubility in water, and the alkylbetaines, sulphobetaines, amidobetaines or amidosulphobetaines.

Amongst these compounds, those which may be mentioned are the products sold under the name MIRANOL, described more particularly in the U.S. Pat. Nos. 2,528,378 and 2,781,354 and classified in the CTFA dictionary, 3rd edition, 1982, under the name amphocarboxyglycinates and amphocarboxypropionates.

These products have the following structures:
amphocarboxyglycinates

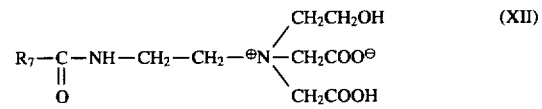 (XII)

in which $R_7$ denotes an alkyl radical derived from copra, or a heptyl, nonyl or undecyl radical;
amphocarboxypropionates

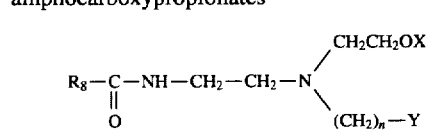 (XIII)

in which:
n denotes 1 or 2;
X denotes the group —$CH_2CH_2COOH$ or hydrogen;

Y denotes —COOH or the radical

—CH—CH$_2$SO$_3$H;
|
OH and

R$_8$ denotes the alkyl radical derived from copra, a C$_7$, C$_9$, C$_{11}$ or C$_{13}$ alkyl radical, a C$_{17}$ alkyl radical and its iso form, an unsaturated C$_{17}$ radical or an alkyl radical derived from linseed oil.

The alkylbetaines are preferably chosen from the (C$_{10}$C$_{20}$)alkylbetaines.

According to the invention, mixtures of surfactants, and in particular mixtures of anionic surfactants and amphoteric, zwitterionic or nonionic surfactants, are preferably used. A particularly preferred mixture is a mixture consisting of an anionic surfactant and a zwitterionic surfactant.

Preferably, an anionic surfactant chosen from sodium (C$_{12}$–C$_{14}$) alkyl sulphates, triethanolamine (C$_{12}$–C$_{14}$) alkyl sulphates or ammonium (C$_{12}$–C$_{14}$) alkyl sulphates, oxyethylenated sodium (C$_{12}$–C$_{14}$) alkyl ethersulphates containing 2.2 moles of ethylene oxide, sodium cocoylisethionate and sodium (C$_{14}$–C$_{16}$)-α-olefinsulphonate, as well as their mixtures, is used with
either an amphoteric surfactant such as an amphocarboxyglycinate defined by the formula (XII), in which R$_7$ denotes an alkyl radical derived from copra, also termed cocoamphocarboxyglycinate and sold by MIRANOL under the name MIRANOL C2M CONC as an aqueous solution containing 38% of active substance;
or a zwitterionic surfactant such as the laurylbetaine sold by HENKEL under the name DEHYTONAB 30 as an aqueous solution containing 32% of active substance.

The silicones are used in the compositions according to the invention in proportions of between 0.2 and 20% by weight relative to the total weight of the composition, and preferably between 0.2 and 10% by weight.

The scleroglucans are used in proportions sufficient to ensure the homogeneity and thickening of the compositions of the invention, and preferably in proportions of between 0.1 and 5% by weight, and in particular between 0.2 and 3% by weight, relative to the total weight of the composition.

The surfactants are used in the compositions according to the invention in proportions sufficient to confer a detergent character on the composition, and preferably of between 5 and 50% by weight relative to the total weight of the composition, and in particular between 8 and 30% by weight.

When the amphoteric or zwitterionic surfactants are used as a mixture with the anionic surfactants they represent up to 50%, and preferably 5 to 30%, by weight of the total weight of the amount of surfactants present in the composition.

When the nonionic surfactants are used as a mixture with the anionic surfactants they represent up to 90%, and preferably 5 to 50%, by weight of the total weight of the amount of surfactants present in the composition.

The pH of the compositions according to the invention is generally between 3 and 9 and preferably between 4 and 8.

The aqueous medium can consist solely of water or of a mixture of water and a cosmetically acceptable solvent, such as C$_1$–C$_4$ lower alcohols, such as ethanol, isopropanol or n-butanol; alkylene glycols, such as ethylene glycol, or glycol ethers.

In addition to the combination defined above, the compositions according to the invention may contain viscosity regulators, such as thickeners, electrolytes and hydrotropic agents, amongst which sodium chloride and sodium xylenesulphonate may be mentioned.

The viscosity regulators are used in the compositions according to the invention in proportions ranging up to 6% by weight relative to the total weight of the composition.

The compositions according to the invention may optionally also contain other agents having the effect of improving the cosmetic properties of hair and the skin, provided that they do not alter the stability of the compositions. It is possible to use, for example, cationic surfactants, anionic or cationic or amphoteric polymers or optionally quaternized proteins.

The compositions may also contain various adjuvants customarily used in cosmetics, such as perfumes, preservatives, sequestering agents, foam stabilizers and acidifying agents or agents for rendering alkaline which are well known in cosmetics.

The compositions according to the invention are more particularly used as shampoos for washing and conditioning hair and they are applied, in this case, to wet hair in effective amounts for washing it, this application being followed by rinsing.

The compositions according to the invention can also be used as shower gels for washing hair and the skin, in which case they are applied to the wet skin and hair and rinsed off after application.

The following examples are intended to illustrate the invention without implying any limitation.

EXAMPLE 1

A shampoo of the following composition is prepared:

| | |
|---|---|
| scleroglucan sold under the name ACTIGUM CS 11 by SANOFI BIO INDUSTRIES, containing 90% AS | 0.9 g AS |
| sodium xylenesulphonate sold under the name ELTESOL SX 93 by MARCHON, containing 93% AS | 1.86 g AS |
| mixture of two PDMS of different viscosities, sold under the name CF 1241 by GENERAL ELECTRIC | 3.0 g AS |
| laurylbetaine sold under the name DEHYTON AB 30 by HENKEL as an aqueous solution containing 32% AS | 2.0 g AS |
| triethanolamine (C$_{12}$–C$_{14}$/70–30) alkyl sulphate as an aqueous solution containing 40% AS | 10.0 g AS |
| preservative qs | |
| sodium chloride | 4.0 g |
| water qs | 100.0 g |

Hair washed with this shampoo is easy to comb, has a sheen and is soft to the touch.

EXAMPLE 2

A shampoo of the following composition is prepared:

| | |
|---|---|
| scleroglucan sold under the name ACTIGUM CS 11 by SANOFI BIO INDUSTRIES, containing 90% AS | 0.9 g AS |
| ammonium lauryl sulphate | 8.0 g AS |
| silicone DC 200-350 CSt sold by DOW CORNING | 3.0 g |
| HCl qs pH = 5 | |
| water qs | 100.0 g |

EXAMPLE 3

A shampoo of the following composition is prepared:

| | |
|---|---|
| scleroglucan sold under the name ACTIGUM CS 11 by SANOFI BIO INDUSTRIES, containing 90% AS | 1.35 g AS |
| mixture of a dimethiconol and a cyclomethicone sold under the name Q2 1401 by DOW CORNING | 5.0 g AS |
| triethanolamine ($C_{12}$–$C_{14}$/70–30) alkyl sulphate as an aqueous solution containing 40% AS | 2.0 g AS |
| oxyethylenated sodium ($C_{12}$–$C_{14}$) alkyl ether-sulphate containing 2.2 moles of ethylene oxide sold as 25% AS | 10.0 g AS |
| preservative, perfume, qs | |
| HCl qs pH = 6.4 | |
| water qs | 100.0 g |

EXAMPLE 4

A shampoo of the following composition is prepared:

| | |
|---|---|
| scleroglucan sold under the name ACTIGUM CS 11 by SANOFI BIO INDUSTRIES, containing 90% AS | 0.9 g AS |
| silicone DC 593 sold by DOW CORNING | 0.5 g |
| laurylbetaine sold under the name DEHYTON AB 30 by HENKEL as an aqueous solution containing 32% AS | 2.0 g AS |
| triethanolamine ($C_{12}$–$C_{14}$/70–30) alkyl sulphate as an aqueous solution containing 40% AS | 10.0 g AS |
| preservative, perfume, qs | |
| triethanolamine qs pH = 6.8 | |
| water qs | 100.0 g |

Hair washed with this shampoo is easy to comb, has a sheen and is soft to the touch.

EXAMPLE 5

A shampoo of the following composition is prepared:

| | |
|---|---|
| scleroglucan sold under the name ACTIGUM CS 11 by SANOFI BIO INDUSTRIES, containing 90% AS | 2.25 g AS |
| poly(hydroxypropyl ether) nonionic surfactant prepared by a condensation reaction, under alkaline catalysis, of 3.5 moles of glycidol with an alpha-diol having 12 carbon atoms, in accordance with the process described in the Patent FR-A-2,091,516 | 5.0 g AS |
| sodium ($C_{14}$–$C_{16}$) olefinsulphonate | 5.0 g AS |
| SILBIONE 70641 V 200 oil sold by RHONE POULENC | 3.5 g |
| preservative, perfume, qs | |
| HCl qs pH = 7 | |
| water qs | 100.0 g |

EXAMPLE 6

A shower gel of the following composition is prepared:

| | |
|---|---|
| scleroglucan sold under the name AMIGEL by ALBAN MULLER INTERNATIONAL | 1.5 g AS |
| oxyethylenated sodium ($C_{12}$–$C_{14}$) alkyl ether-sulphate containing 2.2 moles of ethylene oxide, sold as 25% AS | 8.0 g AS |
| cocoamphocarboxyglycinate sold under the name MIRANOL C2M CONC by MIRANOL, as an aqueous solution containing 38% AS | 5.0 g AS |
| RHODORSIL 763 oil sold by RHONE POULENC | 0.5 g |
| preservative, perfume, qs | |
| HCl qs pH = 8 | |
| water qs | 100.0 g |

EXAMPLE 7

A shower gel of the following composition is prepared:

| | |
|---|---|
| scleroglucan sold under the name ACTIGUM CS 11 by SANOFI BIO INDUSTRIES, containing 90% AS | 2.7 g AS |
| triethanolamine ($C_{12}$–$C_{14}$/70–30) alkyl sulphate as an aqueous solution containing 40% AS | 8.0 g AS |
| poly(hydroxypropyl ether) nonionic surfactant prepared by a condensation reaction, under alkaline catalysis, of 3.5 moles of glycidol with an alpha-diol having 12 carbon atoms, in accordance with the process described in the Patent FR-A-2,091,516 | 5.0 g As |
| mixture (84/8 by weight) of sodium cocoylisethionate/sodium isethionate sold under the name ARLATONE SCI by ICI | 2.0 g |
| tertiary amine oxide: di(hydroxyethyl)alkyl (copra)-amine oxide sold under the name AROMOX C12 by ARMAK as 50% AS | 1.0 g AS |
| polysiloxane containing a hydroxyalkyl group, of formula: | 2.0 g |

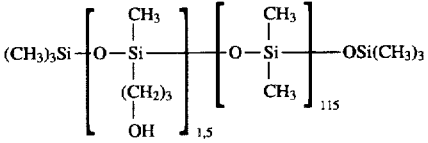

(Mn 9,000)
preservative, perfume, qs
HCl ≈ qs pH = 7
water qs     100.0 g

EXAMPLE 8

A shower gel of the following composition is prepared:

| | |
|---|---|
| oxyethylenated sodium lauryl ether-sulphate containing 2.2 moles of ethylene oxide, sold as 25% AS | 15.0 g AS |
| polydimethylsiloxane sold under the name HUILE SILBIONE 70047 V 300 by RHONE POULENC | 10.0 g |
| cocoamidopropylbetaine as an aqueous solution containing 35% AS, sold under the name TEGOBETAINE HS by GOLDSCHMIDT | 8.0 g AS |
| scleroglucan sold under the name ACTIGUM CS 11 by SANOFI BIO INDUSTRIES, containing 90% AS | 0.27 g AS |
| perfume, preservatives qs | |
| HCl qs pH = 6.5 | |
| water | 100.0 g |

EXAMPLE 9

A shampoo of the following composition is prepared:

| | |
|---|---|
| oxyethylenated sodium lauryl ether-sulphate containing 2.2 moles of ethylene oxide, sold as 25% AS | 13.0 g AS |
| polydimethylsiloxane sold under the name HUILE SILBIONE 47 V 500,000 by RHONE POULENC | 3.0 g |
| cocoamidopropylbetaine as an aqueous solution containing 35% AS, sold under the name TEGOBETAINE HS by GOLDSCHMIDT | 10.0 g AS |
| scleroglucan sold under the name ACTIGUM CS 11 by SANOFI BIO INDUSTRIES, containing 90% AS | 0.27 g AS |
| perfume, preservatives, colorant qs | |
| triethanolamine qs pH = 7 | |
| water | 100.0 g |

I claim:
1. Composition for washing keratinous materials which contains, in an aqueous medium, at least:

one anionic detergent surfactant selected from the group consisting of the alkali metal salts, the ammonium salts, the amine salts and the amino alcohol salts of the following compounds:

alkyl sulphates, alkyl ether-sulphates, alkylsulphonates, alkylsulphosuccinates, alkyl ether-phosphates, acyl sarcosinates, and acyl isethionates, in which the alkyl and acyl radical are a straight hydrocarbon chain of 12 to 18 carbon atoms, and optionally one nonionic or amphoteric detergent surfactant;

one scleroglucan chosen from neutral polysaccharides of microbial origin, obtained by aerobic fermentation of a glucose medium by a Schlerotium and having the structure of a homopolymer of D-glucopyranose and corresponding to the formula:

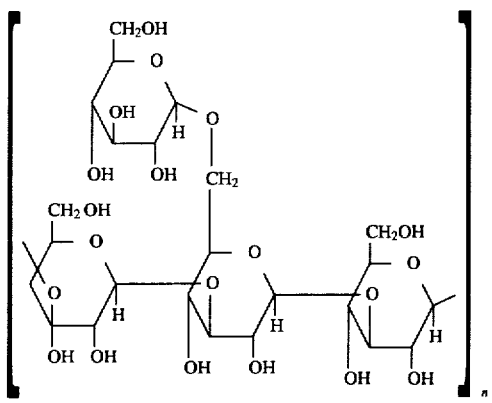

wherein n (degree of polymerization) varies from 500 to 1,600, or said scleroglucan treated with glyoxal;

one nonvolatile silicone insoluble in the aqueous medium selected from the group consisting of:
  (a) polyalkylsiloxanes selected from the group consisting of straight-chain polydimethylsiloxanes containing trimethylsilyl end groups and having a viscosity of $5 \times 10^{-6}$ to 2.5 m$^2$/s at 25° C., and straight-chain polydimethylsiloxanes containing trihydroxysilyl end groups and poly ($C_1$–$C_{20}$) alkylsiloxanes;
  (b) polyalkylarylsiloxanes selected from the group consisting of straight-chain and branched polymethylphenylsiloxanes and polydimethyldiphenylsiloxanes having a viscosity of $10^{-5}$ to $5 \times 10^{-2}$ m$^2$/s at 25° C.;
  (c) silicone gums consisting of polydiorganosiloxanes having a high molecular weight of between 200,000 and 1,000,000, used on their own or as a mixture in a solvent selected from the group consisting of volatile silicones, polydimethylsiloxane (PDMS) oils, polyphenylmethylsiloxane (PPMS) oils, isoparaffins, methylene chloride, pentane, dodecane, tridecane and tetradecane and their mixtures;
  (d) organopolysiloxane resins which are cross-linked siloxane systems containing $R_2SiO_{2/2}$, $RSiO_{3/2}$ and $SiO_{4/2}$ units, in which units R represents a hydrocarbon group having 1 to 6 carbon atoms or a phenyl group.

2. Composition according to claim 1, wherein the silicone gums are chosen from the poly(dimethylsiloxane/methylvinylsiloxane), poly(dimethylsiloxane/diphenylsiloxane), poly(dimethylsiloxane/phenylmethylsiloxane) and poly-(dimethylsiloxane/diphenylsiloxane/methylvinylsiloxane) gums.

3. Composition according to claim 1, wherein the silicone gums as a mixture in a solvent are chosen from the mixtures of a polydimethylsiloxane hydroxylated at the end of the chain and a cyclic polydimethylsiloxane; a mixture of a polydimethylsiloxane gum with a cyclic silicone; and a mixture of a polydimethylsiloxane gum and a PDMS oil of different viscosities.

4. Composition according to claim 1, wherein the polyorganosiloxanes containing a hydroxyl group are polyorganosiloxanes containing a hydroxyalkyl function, corresponding to the formula:

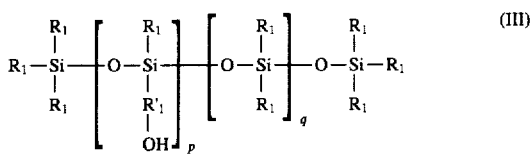

in which:

the radicals $R_1$, which are identical or different, are chosen from methyl and phenyl radicals, at least 60 mole % of the radicals $R_1$ denoting methyl;

the radical $R'_1$ is a $C_2$–$C_{18}$ divalent hydrocarbon alkylene member;

p is between 1 and 30 inclusive; and q is between 1 and 150 inclusive.

5. Composition according to claim 1, in which the nonionic surfactants are chosen from the polyoxyethylenated, polypropoxylated or polyglycerolated alcohols, alkylphenols and fatty acids having a straight fatty chain containing 8 to 18 carbon atoms; the copolymers of ethylene oxide and propylene oxide, the condensation products of ethylene oxide and propylene oxide with fatty alcohols, polyethoxylated fatty amides, polyethoxylated fatty amines, ethanolamides, glycol fatty acid esters, sorbitan fatty acid esters, which may or may not be oxyethylenated, sucrose fatty acid esters, polyethylene glycol fatty acid esters, phosphoric triesters, fatty acid esters of glucose derivatives and amine oxides.

6. Composition according to claim 1, in which the nonionic surfactants are chosen from the compounds corresponding to the following formulae or prepared by the following processes:

a) $R_4O-(CH_2-CH(CH_2OH)-O)_m-H$ (VI)

in which $R_4$ denotes an alkyl radical containing 10 to 14 carbon atoms or a mixture of such radicals and m is an integer or decimal number from 2 to 10;

b) $R_5-CONH-CH_2-CH_2-O-CH_2-CH_2-O-(CH_2-CHOH-CH_2-O)_nH$ (VII) in which $R_5$ denotes an alkyl and/or alkenyl radical having from 11 to 17 carbon atoms, or a mixture of such radicals, and n denotes an integer or decimal number from 1 to 5;

c) $R_6-CHOH-CH_2-O-(CH_2-CHOH-CH_2-O)_p-H$ (VIII) in which $R_6$ denotes an aliphatic, cycloaliphatic or arylaliphatic radical, 7 to 21 carbon atoms, and their mixtures, the aliphatic chains denoting alkyl chains which can contain 1 to 6 ether, thioether and/or hydroxymethylene groups, and p is between 1 and 10 inclusive;

d) the compounds prepared by a condensation reaction, under acid catalysis, of 2 to 10 of glycidol per mole of alcohol or alpha-diol containing 10 to 14 carbon atoms;

e) the poly(hydroxypropyl ether) compounds prepared by polyaddition of glycerol monochlorohydrin to an organic polyhydroxy compound, in the presence of a strong base, with removal of the water by distillation at the rate at which it is formed.

7. Composition according to claim 6, in which the nonionic surfactants are chosen from the compounds corresponding to the formulae:

$C_{12}H_{25}O-(CH_2-CH(CH_2OH)-O)_{4.2}-H$ (IX)

$R_4O-(CH_2-CH(CH_2OH)-O)_{3.75}-H$ (X)

in which $R_4$ denotes a mixture of $C_{10}H_{21}$ and $C_{12}H_{25}$ alkyl radicals;

the compounds prepared by a condensation reaction, under alkaline catalysis, of 3.5 moles of glycidol with an alpha-diol having 12 carbon atoms;

the compounds corresponding to the formula: $R_6-CONH-CH_2-CH_2-O-CH_2-CH_2-O-(CH_2-CHOH-CH_2-O)_{3.5}-H$ (XI) in which $R_6$ denotes a mixture of radicals comprising the following alkyl and alkenyl radicals: $C_{11}H_{23}$, $C_{13}H_{27}$, the radicals derived from copra fatty acids and the radical derived from oleic acid;

the compounds prepared by a condensation reaction of 3.5 moles of glycidol with a mixture of $C_{11}$-$C_{14}$ alpha-diols;

the poly(hydroxypropyl ether) obtained by a condensation reaction of glycerol monochlorohydrin (2.5 moles), in the presence of sodium hydroxide, with dodecane-1,2-diol.

8. Composition according to claim 1, in which the amphoteric and zwitterionic surfactants are chosen from the derivatives of secondary or tertiary aliphatic amines in which the aliphatic radical is a straight or branched chain containing from 8 to 18 carbon atoms and which contain at least one anionic carboxyl, sulphonate, sulphate, phosphate or phosphonate group conferring solubility in water, and the alkylbetaines, sulphobetaines, amidobetaines or amidosulphobetaines.

9. Composition according to claim 8, in which the amphoteric surfactants are chosen from:

the amphocarboxyglycinates corresponding to the formula:

$R_7-C(=O)-NH-CH_2-CH_2-{}^\oplus N(CH_2CH_2OH)(CH_2COO^\ominus)(CH_2COOH)$ (XII)

in which $R_7$ denotes an alkyl radical derived from copra, or a heptyl, nonyl or undecyl radical; and amphocarboxypropionates $R_8-C(=O)-NH-CH_2-CH_2-N(CH_2CH_2OX)((CH_2)_n-Y)$ (XIII)

in which:

n is equal to 1 or 2;

X denotes $-CH_2CH_2COOH$ or hydrogen;

Y denotes $-COOH$ or the radical $-CH(OH)-CH_2SO_3H$;

and $R_8$ denotes the alkyl radical derived from copra, a $C_7$, $C_9$, $C_{11}$ or $C_{13}$ alkyl radical, a $C_{17}$ alkyl radical and its iso form, an unsaturated $C_{17}$ radical or an alkyl radical derived from linseed oil.

10. Composition according to claim 1, which contains a mixture of anionic surfactants and amphoteric, zwitterionic or nonionic surfactants.

11. Composition according to claim 10, wherein the anionic surfactant is chosen from sodium $(C_{12}$-$C_{14})$alkyl sulphates, triethanolamine $(C_{12}$-$C_{14})$alkyl sulphates or ammonium $(C_{12}$-$C_{14})$alkyl sulphates, oxyethylenated sodium $(C_{12}$-$C_{14})$alkyl ether-sulphates containing 2.2 moles of ethylene oxide, and sodium cocoylisethionate, as well as their mixtures and wherein it is used with either an amphoteric surfactant chosen from the ampho-carboxyglycinates;

or the zwitterionic surfactants of the family of the alkylbetaines.

12. Composition according to claim 1, in which the silicones are present in the composition in proportions of between 0.2 and 20% by weight relative to the total weight of the composition.

13. Composition according to claim 1, in which the scleroglucans are used in proportions of between 0.1 and 5% by weight.

14. Composition according to claim 1, in which the surfactants are used in proportions of between 5 and 50% by weight relative to the total weight of the composition.

15. Composition according to claim 1, in which a mixture of anionic surfactants and amphoteric or zwitterionic surfactants is used in which the amphoteric or zwitterionic surfactants represent up to 50% by weight relative to the total weight of the surfactants present in the composition.

16. Composition according to claim 1, in which a mixture of nonionic surfactants and anionic surfactants is used and in which the nonionic surfactants represent up to 90% by weight relative to the total amount of surfactants present in the composition.

17. Composition according to claim 1, which has a pH of between 3 and 9.

18. Composition according to claim 1, which contains viscosity regulators chosen from electrolytes, hydrotropic agents and thickeners other than the scleroglucans.

19. Composition according to claim 1 which also contains anionic, cationic or amphoteric polymers or proteins.

20. Procedure for washing and conditioning hair, wherein the composition as defined in claim 1 is applied to wet hair and rinsing with water is then carried out.

21. Procedure for washing the skin, in which a shower gel having the composition as defined in claim 1 is applied to the skin and rinsing with water is then carried out.

22. Composition according to claim 1, wherein the anionic surfactant is selected from the group consisting of triethanolamine $(C_{12}-C_{14})$ alkyl sulphates, ammonium $(C_{12}-C_{14})$ alkyl sulphates, oxyethylenated sodium $(C_{12}-C_{14})$ alkylether sulphates and sodium cocoylisethionate/sodium isethionate.

23. Composition according to claim 1, wherein the anionic surfactant is selected from the group consisting of triethanolamine $(C_{12}-C_{14})$ alkyl sulphates, ammonium $(C_{12}-C_{14})$ alkyl sulphates, and oxyethylenated sodium $(C_{12}-C_{14})$ alkylether sulphates.

* * * * *